(12) United States Patent
Grange et al.

(10) Patent No.: US 11,672,943 B2
(45) Date of Patent: Jun. 13, 2023

(54) SLEEP AID DEVICE

(71) Applicant: HELIGHT, Meyzieu (FR)

(72) Inventors: Jérôme Armand Joseph Grange, Saint Etienne (FR); Jean Marc Moncorger, Lyons (FR); Julien Michel Thevenet, Saint Sorlin de Morestel (FR); Didier Denis Felix, Corbelin (FR); Claude Gronfier, Lyons (FR)

(73) Assignee: HELIGHT, Meyzieu (FR)

( * ) Notice: Subject to any disclaimer, the term of this patent is extended or adjusted under 35 U.S.C. 154(b) by 226 days.

(21) Appl. No.: 16/337,143

(22) PCT Filed: Sep. 27, 2017

(86) PCT No.: PCT/FR2017/052621
§ 371 (c)(1),
(2) Date: Mar. 27, 2019

(87) PCT Pub. No.: WO2018/060616
PCT Pub. Date: Apr. 5, 2018

(65) Prior Publication Data
US 2020/0030569 A1    Jan. 30, 2020

(30) Foreign Application Priority Data
Sep. 28, 2016   (FR) ...................................... 1659221

(51) Int. Cl.
*A61M 21/02* (2006.01)
*A61M 21/00* (2006.01)

(52) U.S. Cl.
CPC ..... *A61M 21/02* (2013.01); *A61M 2021/0044* (2013.01); *A61M 2205/50* (2013.01);
(Continued)

(58) Field of Classification Search
CPC .......... A61M 21/02; A61M 2021/0044; A61M 2205/50; A61M 2205/8206; A61M 2205/8237; A61M 2210/04
(Continued)

(56) References Cited

U.S. PATENT DOCUMENTS 5,715,214 A * 2/1998 Svarnias ................ G04C 23/00
200/38 R
6,554,439 B1 * 4/2003 Teicher ................... F21S 10/02
362/2
(Continued)

FOREIGN PATENT DOCUMENTS

DE     102012004647 A1   9/2013
WO     2012/137159 A1    10/2012

OTHER PUBLICATIONS

English Machine Translation of DE102013208905 (see attached),Nov. 20, 2014, Kunz Dieter (Year: 2014).*
(Continued)

*Primary Examiner* — Sunita Reddy
(74) *Attorney, Agent, or Firm* — Nath, Goldberg & Meyer; Joshua B. Goldberg (57) ABSTRACT

The invention concerns a device for helping a user fall asleep, comprising a light source designed to emit a substantially monochromatic red or quasi-monochromatic light encouraging the user to fall asleep, characterized in that it comprises a control unit designed to automatically control said light source according to a predefined law according to which the light power emitted by said light source decreases gradually over time in such a way as to change automatically between a maximum power value and a minimum power value, the light power emitted by said light source at a given time always being greater than or equal to the light power emitted at a subsequent time.

22 Claims, 4 Drawing Sheets

(52) U.S. Cl.
CPC ............... *A61M 2205/8206* (2013.01); *A61M 2205/8237* (2013.01); *A61M 2210/04* (2013.01)

(58) Field of Classification Search
USPC .................................................. 600/26–28
See application file for complete search history.

(56) References Cited

U.S. PATENT DOCUMENTS

| | | | |
|---|---|---|---|
| 7,280,439 B1* | 10/2007 | Shaddox | F21V 33/0052 362/1 |
| 9,762,056 B1* | 9/2017 | Miller | H01R 25/003 |
| 2003/0062856 A1* | 4/2003 | Yano | H05B 39/044 315/291 |
| 2003/0156416 A1* | 8/2003 | Stopa | F21V 5/04 362/294 |
| 2003/0231495 A1 | 12/2003 | Searfoss, III | |
| 2007/0083079 A1* | 4/2007 | Lee | A61M 21/00 600/27 |
| 2008/0091250 A1* | 4/2008 | Powell | H05B 45/20 607/90 |
| 2010/0130812 A1* | 5/2010 | Martel | A61M 21/02 600/27 |
| 2010/0331930 A1* | 12/2010 | Burgmann | A61N 5/0613 607/89 |
| 2011/0010014 A1* | 1/2011 | Oexman | F24F 11/0001 700/276 |
| 2011/0084614 A1* | 4/2011 | Eisele | H05B 47/105 315/152 |
| 2011/0215725 A1* | 9/2011 | Paolini | H05B 45/24 315/153 |
| 2012/0137406 A1* | 6/2012 | Hide | A61F 9/04 2/206 |
| 2012/0206050 A1* | 8/2012 | Spero | F21K 9/232 315/152 |
| 2013/0184516 A1* | 7/2013 | Genereux | A61N 5/0618 600/28 |
| 2014/0233243 A1* | 8/2014 | Cieplik | F21V 3/0625 362/311.02 |
| 2016/0008568 A1* | 1/2016 | Attia | A61B 5/486 600/28 |
| 2016/0015315 A1* | 1/2016 | Auphan | A61B 5/6892 600/301 |
| 2016/0158486 A1* | 6/2016 | Colbaugh | A61N 5/0618 607/88 |
| 2017/0224951 A1* | 8/2017 | Weber | A61M 21/02 |
| 2017/0252533 A1* | 9/2017 | Genereux | A61M 21/02 |

OTHER PUBLICATIONS

English Translation of WO2012137159A1, Grounauer, Pierre-Alain (see attached) (Year: 2012).*

* cited by examiner

SLEEP AID DEVICE

This is a National Phase Application filed under 35 U.S.C. 371 as a national stage of PCT/FR2017/052621, filed Sep. 27, 2017, an application claiming the benefit of French Application No. 1659221, filed Sep. 28, 2016, the content of each of which is hereby incorporated by reference in its entirety.

TECHNICAL FIELD

The present invention relates to the general field of sleep induction, and especially to sleep-inducing devices that emit light.

More particularly, the invention relates to a device for inducing sleep in a user, comprising a light source designed to emit a substantially monochromatic or almost-monochromatic red light favouring the falling asleep of the user.

The invention also relates to a system for inducing sleep in a user comprising a sleep-inducing device.

The invention also relates to a method for inducing sleep in a user, wherein a user is subjected to a monochromatic red light favouring the falling asleep of the user, from a light source.

PRIOR ART

It is known that light, and in particular white light, has a great influence on the human circadian rhythms and in particular on the sleep. Indeed, the human natural sleep rhythm normally substantially follows that of sun, so as to be awake during the day and to sleep during the night.

More precisely, it is known that the human sleep, and hence the good progress of the circadian rhythm, depends in particular on the pineal gland (or epiphysis) and on the hormone it secretes, the melatonin. Indeed, this hormone is known to regulate the human biologic rhythms, including the sleep. In particular, it is known that certain components of the light visible by the human eye (i.e. the white light) are liable to upset the good functioning of this gland and in particular to block the production of melatonin, as for example blue light. Conversely, it is known that red light has no or very little influence on the production of this hormone, and is hence almost without influence on the human circadian rhythm.

In order not to disturb the human circadian rhythm, it has been proposed to use lighting devices emitting a red light that has no or little influence on the production of melatonin and hence on a good progress of sleep. It is known in particular to use such devices in places intended for sleeping but in which it is however necessary to guarantee a certain level of lighting, in particular to allow a safe displacement, without disturbing too much the sleep.

Hence, it is for example known to use such lighting devices in a domestic environment, in a house, for example in a chamber, a corridor, stairs, or even a refrigerator. Indeed, when an occupant of the so-equipped house wakes up during the night and wants to get around, he/she can use the lighting provided by the known devices to safely move around without having to use the traditional lighting of the house. Hence, the user is preserved from the white light (and from its components, in particular the blue ones, which are harmful for his/her circadian rhythm) and can hence more easily fall back asleep.

The known devices are often equipped with motion sensors to detect the displacement of the user and hence light up upon passage thereof, then automatically light off when the user no longer moves. In order to optimize the energy consumption of these known devices, these latter may also be equipped with light sensors, in order to come into operation only when the dark is complete.

The known devices generally give satisfaction to their users, by securing the potential night displacements thereof while limiting the impact to their falling back asleep.

However, these known devices are limited to this dual function of securing the displacements and preserving the falling back asleep, and are not adapted to favour the initial falling asleep itself, i.e. to contribute directly, effectively, and positively, to the passage from the awake state to the unconscious sleep state, in particular at the beginning of the night sleep phase.

On the contrary, these devices must not be placed in a bedroom, for example, because they could disturb the initial falling asleep by subjecting the user to untimely light-up/light-off cycles, accidentally operated by possible moves (voluntary or unconscious) of the user during his/her sleep, liable to trigger the motion sensors equipping the known lighting devices in question.

DISCLOSURE OF THE INVENTION

The objects assigned to the present invention hence aim to remedy the various drawbacks exposed hereinabove and to propose new device and system for inducing sleep in a user that, while being particularly efficient for inducing sleep in a user, are very simple in design and not expensive.

Another object of the invention aims to propose new sleep-inducing device and system that allow contributing efficiently to the falling asleep of each user by adapting to his/her fall-asleep characteristics.

Another object of the invention aims to propose new sleep-inducing device and system that allow contributing to the good regulation of the circadian rhythm of the human sleep.

Another object of the invention aims to propose new sleep-inducing device and system that aim not to disturb the production of melatonin.

Another object of the invention aims to propose new sleep-inducing device and system that are particularly energy-efficient.

Another object of the invention aims to propose new sleep-inducing device and system that are beneficial for the organism, even in an environment that is not totally dark.

Another object of the invention aims to propose new sleep-inducing device and system that can be used in a plurality of different places.

Another object of the invention aims to propose new sleep-inducing device and system that are particularly simple to use.

Another object of the invention aims to propose new sleep-inducing device and system that are particularly intuitive, ergonomic and playful to use.

Another object of the invention aims to propose new sleep-inducing device and system that are particularly compact, robust and reliable.

Another object of the invention aims to propose new sleep-inducing device and system that are easily transportable.

Another object of the invention aims to propose new device and system for inducing sleep in a user that are particularly effective and efficient.

Another object of the invention aims to propose new device and system for inducing sleep in a user that are particularly simple, intuitive, ergonomic and playful to use.

Another object of the invention aims to propose a new sleep-inducing method that is particularly effective and efficient.

Another object of the invention aims to propose a new sleep-inducing method that is adapted to a plurality of users.

Another object of the invention aims to propose a new sleep-inducing method that allow contributing to the good regulation of the circadian rhythm of the human sleep.

Another object of the invention aims to propose a new sleep-inducing method that aims not to disturb the production of melatonin.

The objects assigned to the invention are achieved by means of a device for inducing sleep in a user, comprising a light source designed to emit a substantially monochromatic or almost-monochromatic red light favouring the falling asleep of the user, characterized in that it comprises a control unit designed to automatically control said light source in accordance with a predefined law according to which the light power emitted by said light source progressively decreases over time so as to evolve automatically between a maximum power value and a minimum power value, the light power emitted by said light source at one moment being always higher than or equal to the light power emitted at a later moment.

The objects assigned to the invention are achieved by means of a system for inducing sleep in a user, comprising a device according to the preceding one, as well as a remote control terminal that integrates said law modification and/or creation means, said remote control terminal being designed to communicate with a remote communication module of said device.

The objects assigned to the invention are also achieved by means of a method for inducing sleep in a user, wherein a user is subjected to a monochromatic red light favouring the falling asleep of the user, from a light source, characterized in that the light power emitted by said light source is automatically and progressively decreased over time so that said power automatically evolves between a maximum light power value and a minimum power value that is preferably substantially null, the light power emitted by said light source at one moment being always higher than or equal to the light power emitted at a later moment.

BRIEF DESCRIPTION OF THE DRAWINGS

Other features and advantages of the invention will appear and be revealed in more detail in the following description, made with reference to the appended drawings and given by way of purely illustrative and non-limitative example, in which.

BEST WAY TO IMPLEMENT THE INVENTION

The invention relates as such to a device for inducing sleep in a user. Said device preferably comprises an apparatus, a means, a tool, a machine, an instrument, etc., that is advantageously designed to help a user in falling asleep, or at least in having a rest, by advantageously providing the room in which the user is with a lighting particularly suitable for sleep and/or rest. Preferentially, said lighting is a lighting visible by the human eye and advantageously a lighting that appears red to him/her, as will be described hereinafter.

Preferentially, the user of the apparatus is a human, of any age and any sex. By extension and without departing from the framework of the invention, the user may also denote an animal, at least certain body properties of which, and in particular certain cutaneous and/or optical features of which, are roughly close to those of human beings.

Preferably, said device is a photomodulation or photobiomodulation device, i.e. a device capable of emitting a particular light for different indications, and in particular for favouring the falling asleep and/or the rest, as will be described in detail hereinafter. Said device is then advantageously intended to interact, through the light it emits, with the light-receptor cells located in the eye or on the skin of the user.

Figure 6:
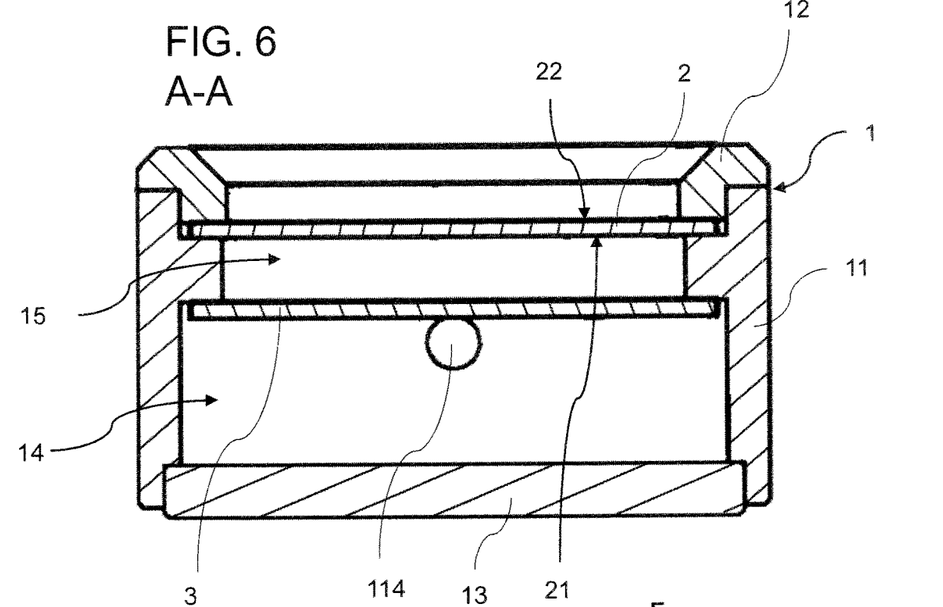
FIG. 6 is a sectional view of the sleep-inducing device of FIG. 4.
Figures 7, 8:
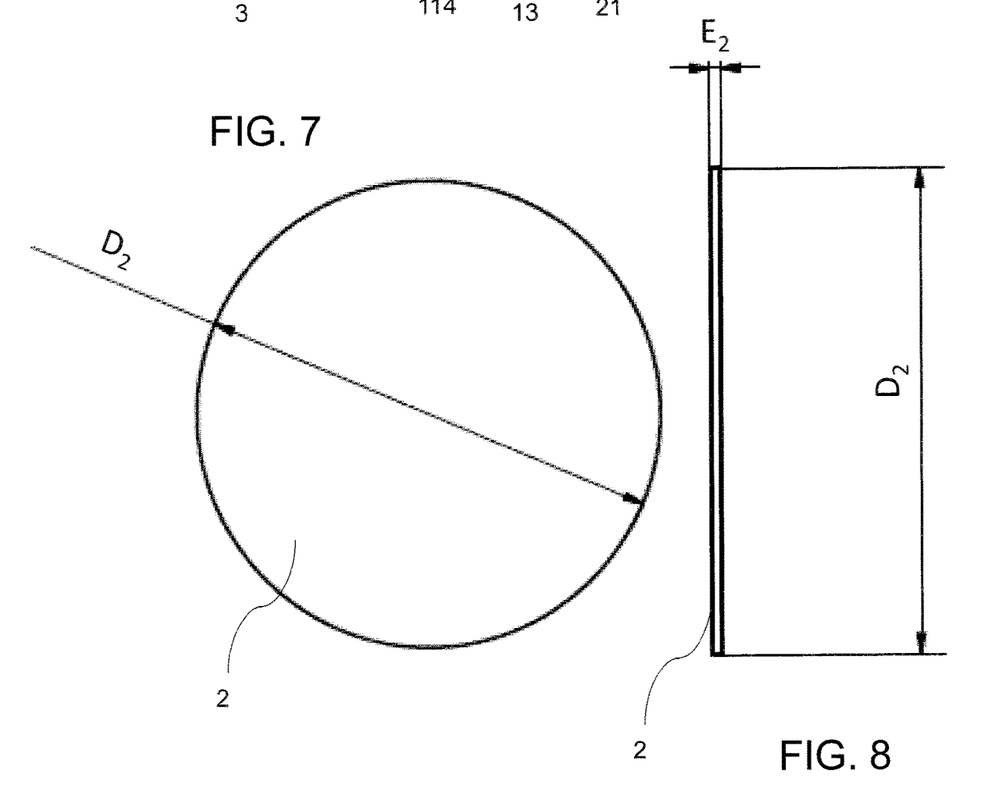
FIG. 7 is a top view of the diffuser equipping the sleep-inducing device of FIG. 1.
FIG. 8 is a side view of the diffuser of FIG. 7.

According to the invention, said device comprises a light source 3 or possibly a plurality of light sources 3, as can be seen for example in FIG. 6. Said light source 3 is advantageously formed by any light source, i.e. any element, means, device or set of components designed to emit light, as for example a bulb, and for example an incandescence bulb, a fluorescent bulb, a halogen bulb, or advantageously a LED bulb (i.e. a bulb composed of one or several light-emitting diodes).

According to the preferential embodiment illustrated in the Figures, said light source comprises at least one light-emitting diode LED, and preferentially a plurality of LEDs, and is preferentially in the form of a LED plate or a LED module, wherein the latter can advantageously be in the form of a disk, as well known as such. In other words, and as can be seen for example in FIG. 6, said light source 3 comprises a LED module, preferentially in the form of a disk, said module being composed of an array of light emitting diodes LEDs, preferentially designed to light up simultaneously so as to produce a light intensity higher than that which would be produced by a single LED. It is hence possible to have a particularly compact and powerful light source 3.

According to the invention, said light source 3 is designed to emit a substantially monochromatic (or almost-monochromatic) red light favouring the falling asleep of the user. Indeed, as said hereinabove, it is known that certain components of the light visible by the human eye, and in particular the red light, have no or little influence on the production of melatonin, one of the natural hormones present in the human body and regulating the human circadian rhythms. Moreover, such a red light is remarkably known not to be toxic for the organism, including for the retina, contrary to the ultraviolet rays, for example.

Hence, said light source 3 emits a light belonging to the spectrum of the visible light, i.e. a light whose wavelength is substantially comprised between 400 nm and 700 nm.

According to the invention, said device is advantageously designed to emit a substantially monochromatic, or almost-monochromatic, or even monochromatic light, i.e. this is a light that advantageously comprises only one wavelength, or at least that tends to have only one wavelength, to within the accuracy inherent to the different components implemented. Advantageously, said wavelength is preferentially comprised between 600 nm and 670 nm, and advantageously between 615 nm and 640 nm, these wavelength ranges corresponding to a red light, the latter having the remarkable advantage to calm the user, to relax him/her, and to help him/her falling asleep.

Advantageously, said light emitted by said light source 3 is a red light whose wavelength is preferably equal to 625 nm+/−15 nm.

Advantageously, the light emitted by said device is a cold light, having a non-ionizing radiation, emitted preferentially by low intensity LEDs (lower than 190 nW/cm$^2$). More particularly, the technical characteristics of the LEDs are advantageously chosen so that the LEDs can transfer energy towards the cells and/or bring signals to the receptor cells located in the eye or on the skin of the user.

According to the invention, said device comprises a control unit designed to automatically control said light source 3. For that purpose, said control unit advantageously comprises one or several elements, means, tools or automatic control devices, as for example and non-limitatively, a calculator, a sensor, a timer, a processor, a memory, etc. In other words, said light source 3 depends on said control unit, so that the latter is in particular capable of controlling, defining, adjusting, verifying, etc., the physical properties of said light source 3, and in particular the power P thereof, without intervention of the user, nor the intervention of any one during the operation of said device.

Still according to the invention, said light source 3 is automatically controlled in accordance to a predefined law L, i.e. in accordance to a model, a cycle or a profile established in advance, for example by the designers of said device. Preferentially, said law L is advantageously recorded into a memory of said control unit, for example during the manufacturing of said device. Said law is then a law according to which the light power P emitted by said light source 3 progressively decreases over time t. In other words, said predefined law L governs the operation that said light source 3 must follow by advantageously controlling at least the power of the latter, and more precisely by progressively and continuously decreasing said power P over time. Advantageously, said predefined law L may be materialized by a mathematical function defining the power P of said light source 3 as a function of time t, as illustrated for example in FIGS. 10 to 13, which will be explained in detail hereinafter. Said power P then automatically and progressively decreases as a function of time t, so that the light power emitted by said light source 3 at one moment T is always higher than the light power emitted at a later moment T+1. In other words, the more time elapses, the more the power emitted by said device decreases. Hence, thanks to said predefined law L, said device operates according to a predefined automatic cycle, the latter being advantageously a cycle of automatic power decrease.

According to the invention, the emitted power P is then controlled by said predefined law L so as to automatically evolve between a maximum power value $P_{max}$ and a minimum power value, as can be seen for example in FIGS. 10 to 13. Preferentially, said minimum power value is a substantially null value. In other words, said predefined law L is such that it will automatically make said power P of said light source 3 pass from a maximum power value $P_{max}$ to a substantially null power, i.e. a power close to zero or even a power equal to zero, and that preferentially according to a predefined and automatic decrease mode, i.e. planned in advance and without intervention of the user. Advantageously, when said device reaches said substantially null power, the latter does no longer emit light. Hence, said device is designed to vary said power P emitted by said light source according to a particular decrease profile defined in advance.

Preferentially, said device comprises a first user interface allowing the user to interact with said device. Said first user interface is then at least designed to allow the user to activate (power on) said device and comprises for example a power-on button, for example a preferentially monostable push-button. In other words, as soon as the user pushes on said power-on button, said device preferentially enters in operation in accordance to said predefined law L. However, it is perfectly conceivable, without departing for the framework of the invention, that said button can be used for other functions, in particular with a long pressure on the latter, as for example for the early power off of said device (i.e. its power off before the end of said predetermined law L) or for triggering a timer, for example, as will be described in detail hereinafter.

Preferentially, said device has a maximum output power $P_{max}$ substantially equal to 40 mW/cm$^2$. In other words, when said device is in operation, the power emitted by said device, and more precisely by said light source 3, is lower than or equal to 40 mW/cm$^2$, so that, once the device is placed on a night stand for example, in normal condition of use, for example at an average distance of 50 cm from the user in lying position, in pre-sleep phase, the receptors of the melanospine type located in the retina are not exposed to a light of more than 400 µW/cm$^2$, for said wavelength, if the user's look is directed towards the light source, this power advantageously corresponding to a threshold power acceptable by the human organism in falling asleep and/or rest phase.

Advantageously, said maximum light power value $P_{max}$ is higher than 600 lux and is advantageously substantially equal to 885 lux. In other words, when said device is in operation, the light power emitted by said device is lower than or equal to 885 lux, this power advantageously corresponding to a threshold power acceptable by the human organism in falling asleep and/or rest phase.

Preferentially, and as illustrated in FIGS. 10 to 13, said maximum power value $P_{max}$ is reached when said device is powered on. In other words, as soon as the user powers said device on, preferentially by means of said power-on button, the light source 3 is called upon and produces its maximum power $P_{max}$. As an alternative, and without departing from the framework of the invention, it is also perfectly conceivable that said maximum power value $P_{max}$ is not reached immediately after said device has been powered on, but rather after a few seconds, for example in order to preserve said light source 3 and/or the energy source thereof (and hence increase the life duration thereof), or even after a few minutes, for example in order to provide a better comfort to the user (in particular in order to avoid any glare of the latter, or to respect his/her personal preferences as will be described in detail hereinafter).

Hence, said device is advantageously designed to accompany the user in his/her falling asleep, and to help him/her to find sleep by diffusing into the room (preferentially in the bedroom) a red light that will progressively and continuously decrease in intensity to finally disappear, said disappearance (or power-off of said light source 3) advantageously intervening after the user has fallen asleep, thanks to said predetermined law L. In other words, said user will be accompanied by the red light of decreasing intensity during his/her falling asleep phase, said red light having almost disappeared advantageously a few minutes after the user has fallen asleep. Hence, thanks to said device and the predefined law thereof, the user is in optimum conditions to fall asleep:

- in a first time, previously to the power-on of said device, the room (bedroom for example) in which the user is lighted by means of the normal light of the room, to allow the user to attend to his/her affairs before going to bed;
- then the device of the invention is powered on and the normal lights are lighted off, so that the room is then illuminated only by the device with a soothing red light;
- the light intensity then decreases automatically, continuously and progressively, so that the ambient luminosity of the room also decreases, so as to progressively place the user in a particularly relaxing and reassuring lighting atmosphere (in particular for people that are afraid of the dark), and to provide a transition between the intensive lighting such as that undergone by the user during the day and the full dark he/she will met once asleep;
- finally, after for example a time laps of about twenty or thirty minutes generally corresponding to the time for falling asleep, the device reaches said substantially null power and the room is then no more illuminated by said device.

Hence, all along this progressive decrease, the user is exposed to the benefits from red light, and that even if the room is not in the dark, as it is the case, for example, in the polar regions or the highly urbanized areas.

Preferentially, said predefined law L is designed so that said light power P decreases substantially continuously as a function of time t between said maximum power value $P_{max}$ and said minimum power value, and advantageously between said maximum power value $P_{max}$ and said substantially null power value, possibly after a constant power plateau where the light power P is constant (preferably equal to said minimum power value) for a predetermined plateau duration.

In other words, the power P is a function of time and said predefined law L preferably comprises a function that is continuous over the interval higher than or equal to zero of said light power P as a function of time t. Hence, said predefined law L preferably follows a mathematical function that is continuous for any time value, it being understood that time t elapses from the moment when said device is powered up (in operation). Advantageously, said function continuously decreases between said maximum power value $P_{max}$, which is its maximum, and said substantially null power, which is preferably its minimum. In other words, said function is preferably a monotonic function in the broad sense (if there are one or several plateaus) or strictly monotonic (if there is no plateau), and decreasing, which means that it only decreases over time (with or without plateau), and it preferentially never increases (in particular after said light power has reached $P_{max}$). In other words, the power P emitted by said light source 3 decreases continuously and progressively, possibly following a constant power plateau during which the power substantially not varies, so that, in this case, the user benefits from a red light of fixed power for a given or chosen duration, then the intensity decreases as a function of the defined or chosen power-off rapidity, without this regular intensity decreasing is preferably affected by a plateau. Hence, advantageously, for the whole duration of use of the sleep-inducing device (i.e. whatever the time t is), said power P only decreases (or stay stable if there are one or several plateaus), automatically and progressively as function of time t, so that the light power emitted by said light source 3 at one moment T is always higher than (or equal to, if there are one or several plateaus) at the light power emitted at a later moment T+1. In other words, the more time t elapses, the more the light power emitted by said device decreases, preferably without ever increasing (in particular after having reached $P_{max}$). As an alternative, it is however conceivable that the predefined law allows no constant power plateau. Hence, thanks to said predefined law L, said power P is advantageously generally (for example, if there are one or several plateaus) and/or strictly (for example, if there is no plateau) decreasing over time t, and it never increases, except for example when the device is powered on, or during a certain time delay after the device has been powered on, and in particular it never increases after having reached said maximum power value $P_{max}$.

Figure 10:
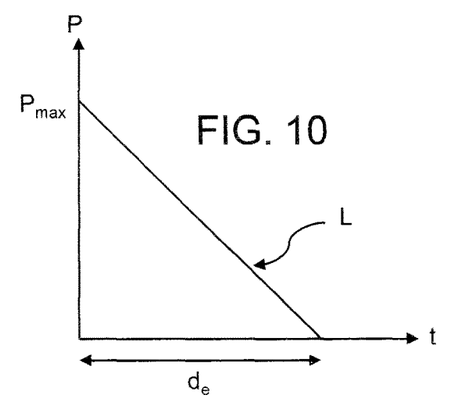
FIGS. 10 to 13 each show a particular example of a predefined law that governs the operation of the device of FIG. 1.
Figure 11:
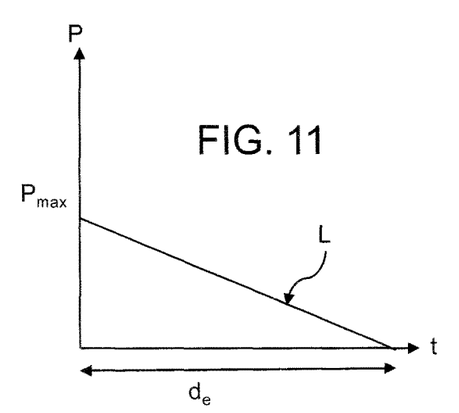

Advantageously, and as illustrated in FIGS. 10 and 11, said function is an affine function, i.e. said predefined law L evolves in a straight line. The directional coefficient of said straight line, i.e. the slope of thereof, is then negative insofar as said function is decreasing and moreover constitutes a significant parameter of said predefined law L. Furthermore, from a mathematical point of view, said maximum power value $P_{max}$ represents the ordinate at the origin of said affine function, i.e. the starting point of said straight line, as can be seen in FIGS. 10 and 11.

Preferentially, said predefined law L is designed so that said light source 3 reaches said minimum power value, and advantageously said substantially null power value, from said maximum power value $P_{max}$ after a predetermined power-off duration $d_e$ has elapsed. In other words, said device is designed to automatically reach its minimum power and preferentially a substantially null power after a certain predefined power-off duration $d_e$, i.e. after a certain time laps defined in advance.

Advantageously, said predetermined power-off duration $d_e$ is comprised between 15 and 40 minutes, for example between 20 and 30 minutes, and is advantageously substantially equal to 30 minutes, which advantageously corresponds to the average falling asleep duration of a human user.

Preferentially, said device comprises a timer designed to automatically count said predetermined power-off duration $d_e$ from the power-on of said device $t_0$. In other words, said device is autonomously capable of automatically calculating the time that elapses from the moment when said device is powered on, preferentially by the user, for example by means of a chronometer, a clock, a counter, etc. or any other means adapted to determine automatically and autonomously the moment at which said power P must be substantially null. Naturally, without departing from the framework of the invention, it is perfectly conceivable that said predetermined power-off duration $d_e$ is not calculated from the power-on of said device but rather from another moment, as for example a moment that would be decided by the user himself/herself and that could correspond to a pressure on a button and for example a second short pressure on said power-on button.

Advantageously, said device comprises a power-off means designed to automatically power said device off at the end of said predetermined power-off duration $d_e$. In other words, said device is advantageously designed to be automatically powered off, i.e. turned off and/or switched off, at the end of said predetermined power-off duration $d_e$, i.e. preferentially when said device reaches said substantially null power. It is hence remarkably possible to save energy, insofar as no component stays in standby mode.

Preferentially, said devices comprises a law modification and/or creation means allowing the user to modify said predefined law L and/or to create a new law. Hence, said device is preferentially designed so that said predefined law L can be modified by the user if he/she wants, in particular so that he/she can adapt it to his/her habits, and in particular his/her sleeping, falling asleep and/or rest habits. As an alternative or as a complement, said device is also advantageously designed to allow the user to create a new law intended to replace said predefined law L. For that purpose, said device comprises one or several elements, tools, devices or means capable of interacting, on the one hand, with the user and, on the other hand, with said device, and more particularly with said control unit, in order to modify and/or replace said predefined law L. Hence, said device comprises for example a second user interface that may include, as an illustration and non-limitatively, one or several buttons, a wheel, a keyboard, a software program, an application, etc.

Advantageously, said law modification and/or creation means is a means for modifying said predetermined power-off duration $d_e$, i.e. that said law modification and/or creation means allows the user to modify said predetermined power-off duration $d_e$. In other words, it is possible for the user to personalize said device and, more particularly, the operation of the latter, by intervening directly on said predefined law L, for example by modifying said predetermined power-off duration $d_e$, i.e. by modifying the power-off time delay of said device and/or the time delay after which said device reaches said null substantially power. As an illustration and non-limitatively, FIG. 11 illustrates a modification of said predetermined power-off duration $d_e$ with respect to FIG. 10, and more precisely a lengthening of this duration, for example in order to make it pass from 22 minutes to 30 minutes, in the case where the user would consider that the initial duration of 22 minutes is too short and does not allow him/her to fall asleep before said device is powered-off. Hence, it is advantageously possible for the user to adapt said predetermined power-off duration $d_e$ to his/her habits and, in particular, to his/her falling asleep time, in particular so that he/she can fall asleep before said device is automatically turned off and/or before said light source 3 has reached said substantially null power. The user can then, in a perfectly remarkable manner, benefit from the red light emitted by said device until he/she is fully asleep, and that whatever the usual duration it takes.

As an alternative or as a complement, said law modification and/or creation means is a means for modifying the maximum power value $P_{max}$, i.e. said law modification and/or creation means allows the user to modify the value of said maximum power $P_{max}$. In other words, it is possible for the user to personalize said device, and more particularly the operation of the latter, by intervening directly on said predefined law L, for example by modifying said maximum power value $P_{max}$, i.e. by modifying the quantity of light that is emitted by said device and, more precisely, by said light source 3. As an illustration and non-limitatively, FIG. 11 illustrates a modification of said maximum power value $P_{max}$ with respect to FIG. 10 and, more precisely, a decrease of the latter, for example in order to make it pass from 885 lux to 500 lux, in the case where the user would consider that the initial maximum power of 885 lux is too high and does not allow him/her to fall asleep and/or to relax. From a mathematical point of view, in the case where said predefined law follows an affine function, the modification of said maximum power value $P_{max}$ amounts to modifying the ordinate at the origin of the straight line. Hence, it is advantageously possible for the user to adapt said maximum power value $P_{max}$ to his/her habits, sensory sensitivities or preferences.

In the particular case where said predefined law L follows a decrease defined by an affine function, it is hence advantageously possible for the user, by modifying said maximum power value $P_{max}$ and/or by modifying said predetermined power-off duration $d_e$, to modify the straight line slope, i.e. to modify the directional coefficient thereof, as can be seen in FIGS. 10 and 11, for example.

Figure 12:
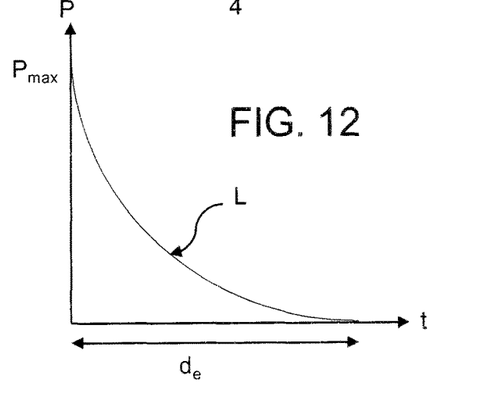
Figure 13:
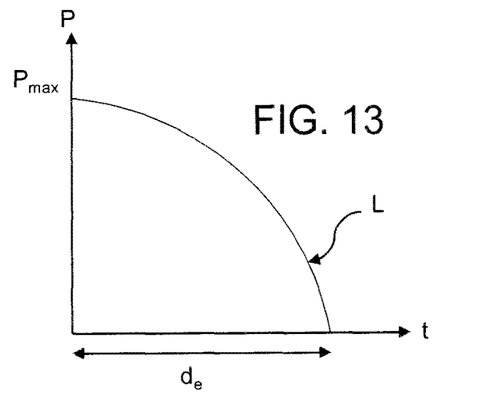

As an alternative or as a complement, it is also perfectly conceivable, without departing from the framework of the invention, that said law modification and/or creation means is a means for modifying the moment when said maximum power value $P_{max}$ is reached, i.e. said law modification and/or creation means allows the user to modify the moment when said maximum power value $P_{max}$ is reached, for example in order to choose another moment than the moment when said device is powered-on, or the decreasing form said predefined law L will follow, as illustrated for example in FIGS. 12 and 13. More precisely, it is perfectly conceivable for the user to modify the affine function of FIG. 10, predefined for example as the basic setting (or factory setting) for said device to transform it into a decreasing curve of convex shape, as that visible in FIG. 12, or into a curve of concave shape, as that visible in FIG. 13, if such a decrease is more adapted to his/her habits and/or personal tastes.

Figure 9:
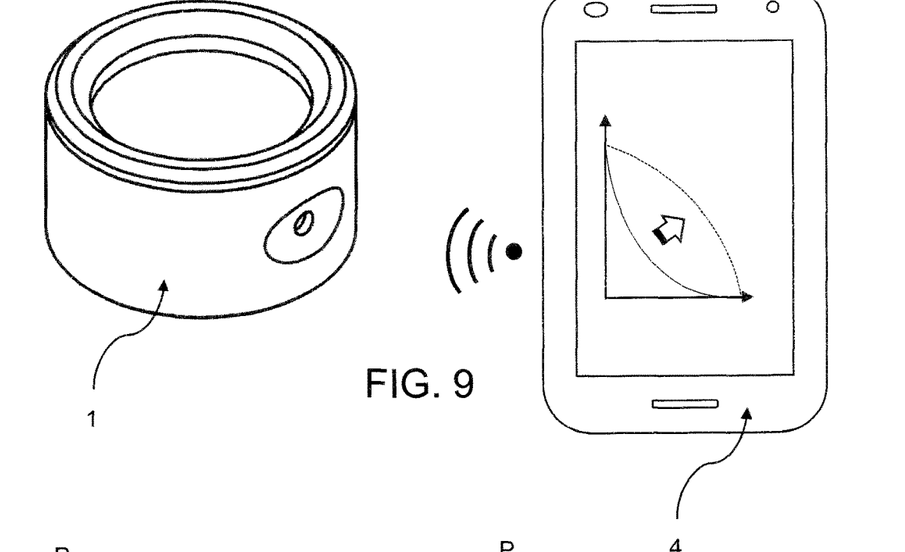
FIG. 9 is a schematic view of a system as described by the invention, said system comprising in particular the device of FIG. 1.

According to the preferential embodiment visible in FIG. 9, said device advantageously comprises a remote communication module as, for example, an antenna, an Ethernet plug, an USB plug, etc. Advantageously, the remote communication module is designed to communicate with a remote control terminal 4 such as a remote controller, a computer, or advantageously a tablet or a smartphone, as illustrated in FIG. 9. In other words, said device is then in communication with said remote control terminal 4, whether it is continuously or punctually, through a wire technology or not, in order to be able to receive information, and preferentially computer data, from said remote control terminal 4. Preferentially, said remote control terminal 4 integrates said law modification and/or creation means, as an application or a software program.

Advantageously, said remote control terminal 4 comprises or forms itself said second user interface that then preferentially comprises a screen and advantageously a touch screen, then allowing the user of said device to easily and intuitively interact with said device through said remote control terminal 4, for example by means of menus, icons, windows or from graphics, as can be seen for example in FIG. 9. Preferentially, and in a manner known per se, said second user interface is controlled by means of an application executed by said remote control terminal.

Preferentially, said communication is a wireless communication as for example a communication of the Bluetooth® type, Wifi® type, etc., well known per se and easily available on the portable remote control terminals of the tablet or smartphone type. In this case, said device then of course comprises a corresponding module adapted to receive and possibly emit signals compatible with the communication protocol used, as for example an antenna.

According to the preferential embodiment visible in the Figures, said device comprises a box 1 inside which is arranged said light source 3. In other words, said device comprises a casing of envelope intended to receive said light source 3. Advantageously, said box is designed for one and/or the other of the following functionalities:

being able to be held in or by hand,
protecting said light source 3, for example from the environment (dust, humidity, object drop, etc.),
maintaining and directing the latter so that the light rays produced by said light source 3 are directed substantially vertically and preferably towards the ceiling of the room in which said device is located,
optimizing the diffusion of the light emitted by said light source 3, for example by comprising a diffuser 2, as will be described in detail hereinafter,
powering said light source, for example by also containing a power supply source, as will be described in detail hereinafter.

Figure 3:
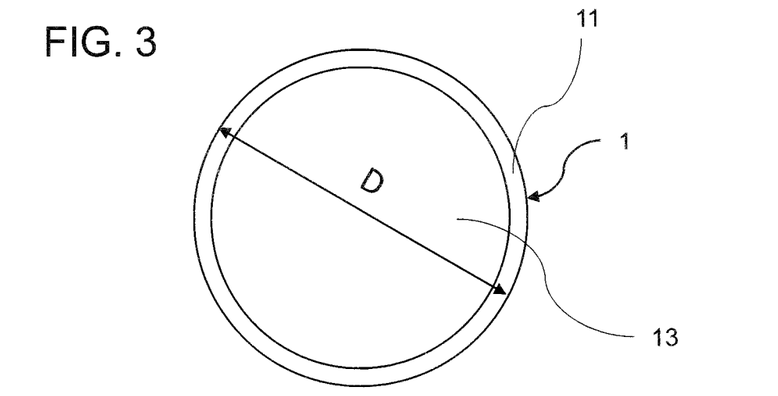
FIG. 3 is a bottom view of the sleep-inducing device of FIG. 1.
Figure 4:
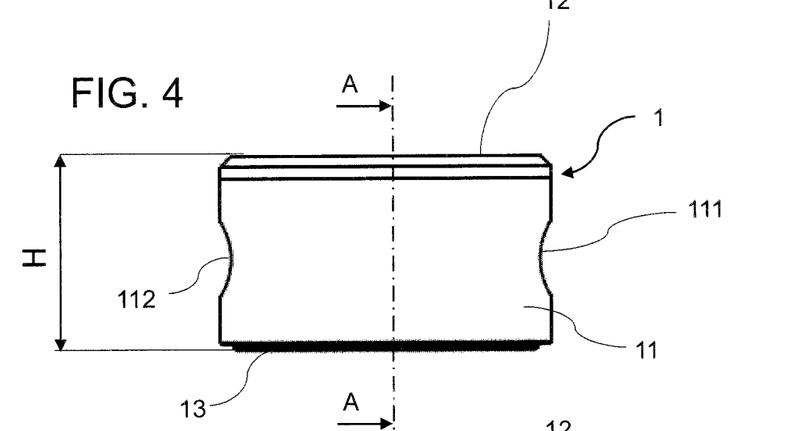
FIG. 4 is a side view of the sleep-inducing device of FIG. 1.
Figure 5:
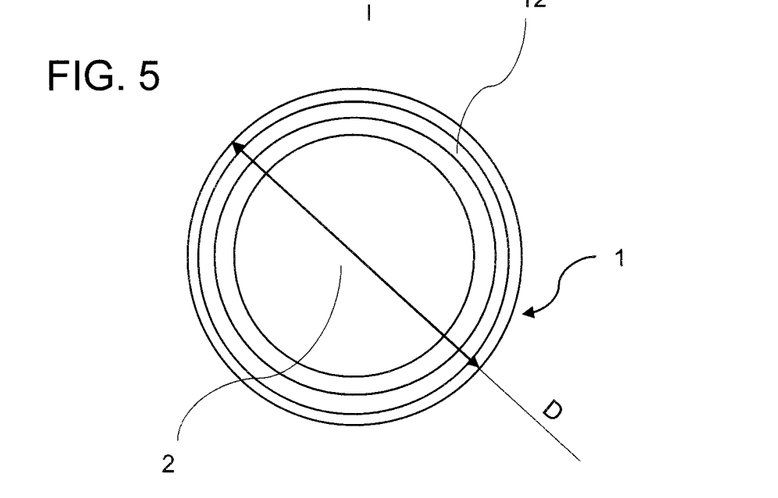
FIG. 5 is a top view of the sleep-inducing device of FIG. 1.

Preferentially, said box 1 is substantially cylindrical in shape and its outer diameter D is preferentially comprised between 50 mm and 80 mm, and is advantageously substantially equal to 70 mm, as illustrated in particular in FIG. 3 or 5, whereas its height H is preferentially comprised between 20 mm and 40 mm and is advantageously substantially equal to 35 mm, as illustrated for example in FIG. 4. Hence, said device is remarkably ergonomic and compact, so that it is easy for the user, on the one hand, to place it anywhere in his/her bedroom, as for example on his/her night stand, and on the other hand, to bring it with him/her, for example during trips where the user does not sleep in his/her usual room, as for example in a hotel room. Hence, thanks to the remarkable compactness of said device, the user will be able to continue benefiting from the red light emitted by said device, including in a hotel room, insofar as said device is particularly adapted to be transported in a travel bag, for example. This optimized transportability of said device is then all the more appreciable for the user since this is generally during travels, when the user does not sleep in his/her usual room, that he/she may most often have difficulties to fall asleep and/or to relax. Moreover, the size of said device is also remarkably adapted to the human ergonomy, and in particular to the human hand, so that it is possible, and even easy for the user, to take said device with only one hand, but also to control it, in particular by means of said first user interface, using only one hand.

Still according to the preferential embodiment visible in the different Figures, said device comprises a diffuser 2 designed to optimize the diffusion of the light emitted by said light source 3, i.e. a means for improving the diffusion of said light.

According to the previously described preferential embodiment, said diffuser 2 advantageously comprises a translucent disk, and/or possibly a transparent disk. In other words, said diffuser 2 forms an optical element designed to improve the diffusion of the light coming from said light source 3. Hence, thanks to said diffuser 2, it is for example possible to improve the homogeneity of the light diffused in the room in which said device is located. Finally, said diffuser 2 is advantageously designed to transform the light rays of said light source 3 into a diffuse and homogeneous light.

In addition to this diffusion function, said diffuser is also advantageously designed to protect said light source, in particular from the environment and from the stresses coming from the latter, as for example dust, water projections, etc., by advantageously forming a protective wall, possibly tight, located above said light source 3. Preferentially, said diffuser 2 forms a part of the upper planar portion of the cylinder formed by said box 1.

Preferentially, the diameter $D_2$ of said diffuser 2 is comprised between 50 mm and 70 mm and is advantageously substantially equal to 62.50 mm, in particular for being able to be inserted into the box 1, whereas its thickness is comprised between 1 and 3 mm and is advantageously substantially equal to 1.5 mm, the latter being particularly adapted to optimally diffuse the light emitted by said light source 3.

More precisely, said diffuser 2 comprises an inner face 21 facing said light source 3 and an opposite, outer face 22, advantageously in contact with the environment. In other words, said diffuser 22 receives the light from said light source 3 through its inner face 21 and diffuse it to the environment through its outer face 22, as can be seen in FIG. 6, for example. Preferentially, and taking into account the implantation of said diffuser 2 in the box 1, said inner face 21 is the lower face and said outer face 22 is the upper face. Advantageously, said inner face 21 has a smoother state of surface than the state of surface of said outer surface 22, which allows, in a remarkable manner, optimizing the diffusion of said light. In other words, said inner and outer faces 21, 22 of said diffuser have not the same state of surface so as to optimize and improve the diffusion of the light emitted by said light source. More precisely, said inner face 21 receiving the light has a state of surface that is relatively smooth, whereas said outer face 22 diffusing the light has a state of surface that is relatively granular.

Advantageously, said diffuser 2 is made of a material comprising at least polycarbonate and a diffusing product, in particular in order to modify the natural properties of transparency of the polycarbonate. As an alternative, or as a complement, other materials can be used to make said diffuser 2, without departing from the framework of the invention, as for example poly(methylmethacrylate) (PMMA), polyester (PES), or polyepoxide, these materials being preferentially combined with a diffusing product.

Preferentially, said box 1 comprises a main body 11 formed of a cylindrical tube portion, as can be seen in FIGS. 1 to 6, said main body 11 being designed to receive said diffuser 2.

According to the preferential embodiment, visible in particular in FIG. 6, said box 1, and more precisely said main body 11, comprises a diffusion compartment 15 itself comprising said diffuser 2. Preferentially, said diffusion compartment 15 is in the form of a cavity, advantageously cylindrical, located between said diffuser 2 and said light source 3 inside which said light emitted by said light source 3 circulates.

Preferentially, said box 1 comprises a lid 12 designed to interact, on the one hand, with said main body 11 and, on the other hand, with said diffuser 2. More precisely, as can be seen in FIG. 6, said lid 12 is designed to hold said diffuser 2 in place within said main body 11 while letting the light coming from said diffuser 2 pass through. For that purpose, said lid 12 is preferentially in the form of a non-removable ring, crimped with an O-ring at the upper end of said main body 11 above said diffuser 2, as can be seen in FIG. 6. More precisely, said lid 12 is then advantageously equipped with a thread designed to correspond with a tap formed inside said main body 11. Advantageously, as can be seen in FIG. 6, said diffuser 2 is then in rest against a shoulder of said main body 11 so that the diffuser 2 is totally immobilized. Preferably, said lid 12 is non-removable, it being understood that it is alternatively conceivable for it to be removable, for example by means of an unscrewing operation, in order to allow access to said diffuser 2, for example for an operation of cleaning or replacing the latter.

Still according to this same embodiment, said box 1 also comprises a power supply compartment 14 designed to supply said light source 3 with power, this compartment advantageously including an electrical power source, such as a battery or a cell, for example. In other words, said power supply compartment 14 is then advantageously designed to receive a power source for said light source 3, and preferentially an electrical power source. Advantageously, said power source is a rechargeable source, as for example a battery.

Figure 1:
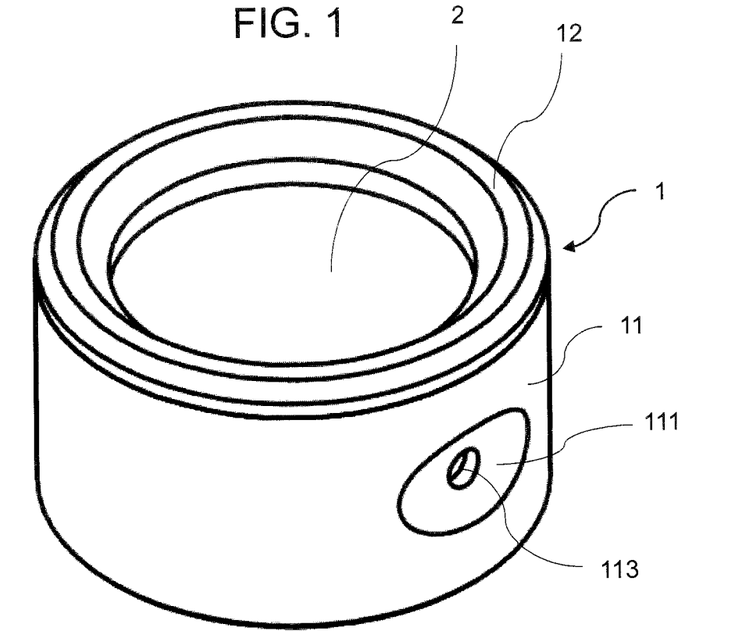
FIG. 1 is a perspective top view of a sleep-inducing device according to a preferential embodiment of the invention.
Figure 2:
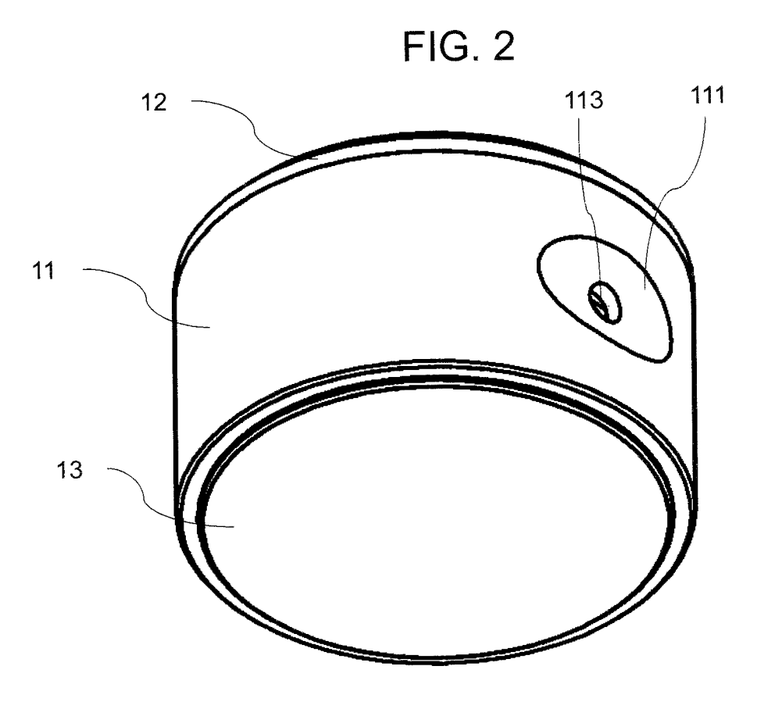
FIG. 2 is a perspective bottom view of the sleep-inducing device of FIG. 1.

Advantageously, and as can be seen in particular in FIGS. 1 and 2, said box 1, and more precisely said power supply compartment 14, comprises a first opening 113 oriented transversally to the cylinder or tube wall of said main body 11. Preferentially, said first opening 113 is designed to receive said first user interface allowing the user to interact with said device and, more precisely, said power-on button. Advantageously, said first opening 113 comprises a circular hole made perpendicular to the cylindrical wall of said box 1.

Preferentially, said first opening 113 is located at the centre of a first counterbore 111 as can be seen in FIGS. 1, 2 and 4, said counterbore 111 being advantageously designed to, on the one hand, improve the ergonomy of the device with respect to the user's digits and, on the other hand, limit the risk that said power-on button is untimely pressed, in particular when said device is in a transport bag.

Advantageously, and as can be seen in FIG. 6, said box 1, and more precisely said power supply compartment 14, comprises a second opening 114 located transversally to the cylinder or tube wall of said main body 11. Preferentially, said second opening 114 is designed to receive a means for recharging said electrical power source, allowing the user to recharge said device and more precisely said electrical power source. As an illustration and non-limitatively, said charging means may comprise a plug of the micro-USB type, connected to a charger that the user can connect to a domestic electrical socket. Advantageously, said second opening 114 comprises a circular hole made perpendicular to the cylindrical wall of said box 1.

Preferentially, said second opening 114 is located at the centre of a second counterbore 112 as can be seen in FIG. 4, said counterbore 112 being advantageously designed to, on the one hand, improve the ergonomy of the device with respect to the user's digits and, on the other hand, limit the risk of deterioration of the connecting components intended to receive said charging means, in particular when said device is in a transport bag.

Advantageously, said first and second openings 113, 114, as well as said associated first and second counterbores 111, 112, are diametrically opposite and are hence symmetrical with respect to the axis of revolution of said box 1.

Preferably, said box 1 comprises a cap 13 designed to close, advantageously rather tightly, said power supply compartment 14, as can be seen in FIG. 2 or 6. Said cap 13 is advantageously non-removable.

Advantageously, said cap 13 is solid and constitutes the base of the cylinder formed by said box 1.

Preferentially, said box 1 is provided with a basement that allows it to stably rest on a planar surface, such as the surface of a night stand, with the light source directed upward, preferentially according to a vertical incidence advantageously directed from the bottom to the top.

Advantageously, and as can be seen in FIGS. 2 and 6, said basement is formed by said cap 13, which is then also designed to serve as a pedestal or base to said device, i.e. it is intended to support at least the weight of said device. Indeed, as can be seen in particular in FIG. 2, said cap 13 will advantageously serve as a bearing surface to put said device on the user's night stand, for example. For that purpose, said cap is preferentially made of a particularly robust material, as for example a plastic material.

Advantageously, and as can be seen in particular in FIG. 6, said power supply compartment 14 and diffusion compartment 15 are coaxial with said light source 3 arranged between each other, which remarkably makes it possible to improve the compactness of said device, in particular by placing said light source between its power supply source and the diffuser 2. In other words, said light source 3 is arranged so as to separate said power supply compartment 14 and diffusion compartment 15 from each other.

The invention also relates as such to a system for inducing sleep in a user comprising a device according to that previously described, as well as a remote control terminal 4 that integrates said law modification and/or creation means, said remote control terminal 4 being designed to communicate with a remote communication module of said device.

The invention also relates as such to a method for inducing sleep in a user, wherein a user is subjected to a monochromatic red light favouring the falling asleep of the user, from a light source 3, characterized in that the light power P emitted by said light source 3 is automatically and progressively decreased over time t so that said power P automatically evolves between a maximum light power value $P_{max}$ and a minimum power value that is preferably substantially null, the light power emitted by said light source 3 at one moment T being always higher than or equal to the light power emitted at a later moment T+1.

Preferentially, said method further comprises a step of modifying said predefined law L and/or creating a new law intended to replace said predefined law L.

POSSIBILITY OF INDUSTRIAL APPLICATION

The invention finds its industrial application in particular in the manufacturing and the use of devices for inducing sleep by means of light.

The invention claimed is:
1. A sleep-inducing device for inducing sleep in a user, the device comprising:
   a light source for emitting a substantially monochromatic or almost-monochromatic red light at a wavelength of 625 nm±15 nm, favoring the falling asleep of the user;
   a control unit configured to automatically control said light source in accordance with a predefined law according to which a light power emitted by said light source progressively decreases over time, evolving automatically between a maximum power value and a minimum power value, the light power emitted by said light source at one moment being always higher than or equal to the light power emitted at a later moment, for the whole duration of use of the sleep-inducing device, said light power never increasing after having reached said maximum power value;

a box, wherein said light source is arranged in said box, said box being provided with a basement that allows the box to stably rest on a planar surface, with the light source directing the red light upwards and away from the user, said predefined law being configured for said light source to reach said minimum power value from said maximum power value after a predetermined power-off duration has elapsed;

a timer configured to automatically count said predetermined power-off duration from a power-on of said device; and a power-off means for automatically powering off said device at an end of said predetermined power-off duration.

2. The sleep-inducing device according to claim 1, wherein said minimum power value is a substantially null value.

3. The sleep-inducing device according to claim 1, wherein said predefined law is designed so that said light power decreases substantially continuously as a function of time between said maximum power value and said minimum power value.

4. The sleep-inducing device according to claim 1, wherein said maximum power value is between 600 lux and 885 lux.

5. The sleep-inducing device according to claim 1, wherein said maximum power value is reached when said device is powered on.

6. The sleep-inducing device according to claim 1, wherein said predetermined power-off duration is between 15 and 40 minutes.

7. The sleep-inducing device according to claim 1, further comprising a law modification and/or creation means, the law modification and/or creation means allowing the user to modify said predefined law and/or to create a new law intended to replace said predefined law.

8. The sleep-inducing device according to claim 7, wherein said law modification and/or creation means allows the user to modify said predetermined power-off duration.

9. The sleep-inducing device according to claim 7, wherein said law modification and/or creation means allows the user to modify the maximum power value and/or a moment when said maximum power value is reached.

10. The sleep-inducing device according to claim 7, further comprising a remote communication module designed to communicate with a remote control terminal that integrates said law modification and/or creation means.

11. The sleep-inducing device according to claim 10, wherein said communication is a wireless communication.

12. A system for inducing sleep in a user, comprising the device according to claim 7, as well as a remote control terminal that integrates said law modification and/or creation means, said remote control terminal being designed to communicate with a remote communication module of said device.

13. The sleep-inducing device according to claim 1, wherein said box is a substantially cylindrical shape.

14. The sleep-inducing device according to claim 13, further comprising a diffuser designed to optimize the diffusion of the light emitted by said light source.

15. The sleep-inducing device according to claim 14, wherein said box comprises a diffusion compartment itself comprising said diffuser, as well as a power supply compartment designed to supply said light source with power, said power supply compartment and diffusion compartment being coaxial with said light source arranged between each other.

16. The sleep-inducing device according to claim 14, wherein said diffuser comprises a translucent disk.

17. The sleep-inducing device according to claim 14, wherein said diffuser comprises an inner face facing said light source and an opposite, outer face, said inner face having a smoother state of surface than the state of surface of said outer surface.

18. The sleep-inducing device according to claim 14, wherein said diffuser is made of a material comprising at least polycarbonate and a diffusing product.

19. The sleep-inducing device according to claim 1, wherein said light source comprises at least one light-emitting diode (LED).

20. A method for inducing sleep in a user, the method comprising:

subjecting a user to a monochromatic red light at a wavelength of 625 nm+/−15 nm, the monochromatic red light being emitted by a light source in order to favor the falling asleep of the user; and automatically and progressively decreasing in accordance with a predefined law, using a control unit, light power emitted by said light source over time, wherein said light power automatically, using said control unit, evolves between a maximum light power value and a minimum power value that is substantially null, wherein the light power emitted by said light source at one moment being always higher than or equal to the light power emitted at a later moment, for the whole duration of use of the light source, said light power never increasing after having reached said maximum power value;

wherein the light source is arranged in a box, said box being provided with a basement that allows the box to stably rest on a planar surface, with the light source directing the red light upwards and away from the user, the predefined law being configured for said light source to reach said minimum power value from said maximum power value after a predetermined power-off duration has elapsed, wherein a timer automatically counts said predetermined power-off duration from a power-on of said light source, and wherein the method further comprises automatically powering off said light source at an end of said predetermined power-off duration.

21. The method for inducing sleep in a user according to claim 20, further comprising a step of modifying a predefined law according to which the light power automatically and progressively decreases over time, and/or creating a new law intended to replace said predefined law.

22. A sleep-inducing device for inducing sleep in a user, the device comprising:

a light source for emitting a substantially monochromatic or almost monochromatic red light at a wavelength of 625 nm±15 nm, favoring the falling asleep of the user;

a control unit configured to automatically control said light source in accordance with a predefined law according to which a light power emitted by said light source progressively decreases over time, evolving automatically between a maximum power value and a minimum power value, the light power emitted by said light source at one moment being always higher than or equal to the light power emitted at a later moment, for the whole duration of use of the sleep-inducing device, said light power never increasing after having reached said maximum power value, wherein the maximum power value is between 600 lux and 885 lux;

a box, wherein said light source is arranged in said box, said box being provided with a basement that allows the box to stably rest on a planar surface, with the light source directing the red light upwards and away from the user, said predefined law being configured for said light source to reach said minimum power value from said maximum power value after a predetermined power-off duration has elapsed;

a timer configured to automatically count said predetermined power-off duration from a power-on of said device; and a power-off means for automatically powering off said device at an end of said predetermined power off duration.

* * * * *